United States Patent [19]

Leung et al.

[11] Patent Number: 5,266,312

[45] Date of Patent: Nov. 30, 1993

[54] METHOD FOR TREATING A STEROID RESISTANT CONDITION VIA ADMINISTRATION OF GAMMA INTERFERON

[75] Inventors: Donald Leung; Stanley Szefler, both of Denver, Colo.

[73] Assignee: National Jewis Center for Immunology and Respiratory Medicine, Denver, Colo.

[21] Appl. No.: 817,577

[22] Filed: Jan. 7, 1992

[51] Int. Cl.$^5$ .................. A61K 37/00; A61K 37/66
[52] U.S. Cl. ...................................... 424/85.5; 530/351
[58] Field of Search ................ 424/85, 5; 530/357

[56] References Cited

U.S. PATENT DOCUMENTS 4,944,941 7/1990 Ammarn ..................... 424/85.1

FOREIGN PATENT DOCUMENTS 8707842 12/1987 World Int. Prop. O. .

OTHER PUBLICATIONS

Kamada, A. K. et al. "Steroid Resistance in Asthma: our current understanding" Pediatric Pulmonology, 00:000-000 (1992) pp. 1-7.

Boguniewicz et al., "Recombinant Gamma Interferon Treatment of Pat. with Atopic Dermatitis," Am. J. Medicine:vol. 88 pp. 365-370 (1990).

Adinoff and Clark, "The Allergic Nature of Atopic Dermatitis", Immunology and Allergy Practice, May, pp. 191/17-28/202 (1989).

Sampson, H. A., "Role of Immediate Hypersensitivity in the Pathogenesis of Atopic Dermatitis", Allergy, vol. 44, Suppl. 9, pp. 52-58 (1989).

Ezekowitz et al., "Partial Correction of the Phagocyte Defect . . . by Subcutaneous Interferon Gamma", NEJM, 319:146-151 (Jul. 21), 1988.

*Primary Examiner*—Howard E. Schain
*Assistant Examiner*—P. Lynn Touzeau
*Attorney, Agent, or Firm*—Felfe & Lynch

[57] ABSTRACT

The invention relates to a method for a steroid resistant condition via administration of gamma interferon to a subject, such as a human, afflicted with the condition. The gamma interferon is administered in an amount sufficient to alleviate at least one parameter associated with the steroid resistant condition.

7 Claims, No Drawings

METHOD FOR TREATING A STEROID RESISTANT CONDITION VIA ADMINISTRATION OF GAMMA INTERFERON

FIELD OF THE INVENTION

This invention relates to the use of inteferon gamma (sometimes referred to as "immune interferon") in the treatment of steroid resistant conditions. More particularly, it relates to the use of interferon gamma in the treatment of conditions which are normally treated by steroids and steroid derivatives, but for which steroid resistant forms of the condition have been observed. The interferon is of particular use in the treatment of steroid resistant allergic conditions, such as asthma and atopic dermatitis.

BACKGROUND OF THE INVENTION

The steroids are a well known and large family of molecules, characterized by a tetracyclic, cyclopenta[α]phenanthrene structure. The family includes hormones, some vitamins, and a number of drugs. Examples of the latter include cortisone and corticosterone.

It is impossible to state a general rule for how therapeutically active steroids function, but they are usually considered to be anti-inflammatory agents—i.e., they interact with receptors in target cells, thereby initiating or interfering with pathways leading to production of molecules involved in an immune response (cytokines, antibodies, stimulatory factors, etc.).

Allergic diseases are among those most commonly treated via administration of steroids, and to a certain extent these drugs are successful. Steroids frequently elicit unwanted side effects, however. In addition, there are subpopulations of subjects who are resistant to treatment with steroids. A comprehensive explanation for why these subpopulations are resistant to steroid treatment and therapy is not known.

The class of molecules referred to collectively as cytokines has become recognized as a potential source of therapeutic agents. One subclass of cytokines are the interferons and interferon derivatives, one of which, gamma interferon or "immune interferon" is the subject of this invention.

Gamma interferon is recognized as a useful therapeutic agent for a number of conditions. U.S. Pat. No. 4,944,94, to Ammann, the disclosure of which is incorporated by reference, teaches that gamma interferon alone or in combination with corticosteroids, can be used to induce individuals afflicted with respiratory disease syndrome (RDS), or idiopathic RDS to produce additional surfactants in the lungs. In a similar manner, PCT application W087/07842, postulates a role for gamma interferon in the treatment of malignant diseases, rheumatic diseases, and allergic diseases. The gamma interferon is used in combination with anti-inflammatory or anti-pyretic agents in the treatment of these diseases and conditions. Additional evidence for a therapeutic role for gamma interferon may be found in Ezekowitz et al., New Eng. J. Med. 319: 146-151 (July, 1988), which teaches the use of subcutaneously administered gamma interferon as a therapy for X-linked chronic granulomatous disease. This study was followed up on in New Eng. J. Med. 324(8): 509-516 (February, 1991), which presents the results of a controlled trial studying the role of gamma interferon in the prevention of infection in chronic granulomatous.

Independent of work on gamma interferon, additional studies have been carried out to study the role of the family of cytokines known as interleukins on the immune system. The mechanism of action by which the class of immunoglobulin known as IgE has been of particular interest, because these immunoglobulins are involved in the allergic response. IgE binds to receptors on the surface of mast cells and basophils, leading to production and release of various molecules. Romagnani, Immunol. Today 11(9): 316-321 (1990), discussed the role of interleukin 4 ("IL-4") on IgE synthesis. The paper discusses how IL-4 and gamma interferon have opposite regulatory effects on IgE production—the former induces synthesis of the IgE, while the latter inhibits it. Vercelli et al., J. Allerg. & Clin. Immunol 88(3): 285-297 (1991), discuss how IL-4 mediates "class switching", i.e., switching of production by B cells from one type of immunoglobulin, such as IgM, to IgE. Boguniewicz et al., Am. J. Med. 88: 365-370 (April 1990), the disclosure of which is incorporated by reference, observed elevated IgE levels in the condition known as atopic dermatitis. Given the role of gamma interferon in inhibiting the effect of IL-4 on IgE stimulation, tests were carried out in which gamma interferon was administered in vivo to patients with atopic dermatitis. At all doses tested, the interferon was linked to a lessening in clinical severity of the disease. These studies are discussed, again, by Jujo et al., Leung et al., and Schneider et al., all at J. All. Clin. Immunol. 87: 383 (1991), all of which are incorporated by reference, which showed (i) that patients with atopic dermatitis had increased IL-4 levels and decreased gamma interferon levels (Jujo); (ii) that one could normalize IL-4 induced proliferative responses by administering gamma interferon (Leung), and (iii) that clinical severity of atopic dermatitis could be reduced by administering the interferon (Schneider). Reinhold et al., Lancet, May 26, 1990, page 1282 confirmed this.

In PCT Application W091/07984 to Leung, the disclosure of which is incorporated by reference, the results discussed supra are summarized in a patent application directed to the treatment of atopic dermatitis and steroid-dependent asthma. "Steroid-dependent asthma" is a condition in which patients afflicted with asthma must take steroid drugs, generally systemically, in order to alleviate the parameters involved with asthma.

Asthma is characterized by several "markers" including increased levels of serum IgE and eosinophils—markers identical to those observed in atopic dermatitis. When the observation set forth in the PCT application was tested in clinical trials involving subcutaneous administration of gamma interferon, however, the results did not show significant clinical improvement in patients with steroid dependent asthma. See, Boguniewicz et al., American Academy of Allergy and Immunology (Abstract, 1992—in press).

The form of asthma known as steroid resistant asthma is caused by unknown mechanisms. It is characterized, however, by persistent T cell activation.

In view of the teachings in the art that gamma interferon is of potential efficacy in treating steroid dependent asthma, it is surprising to find that it is effective against steroid resistant conditions such as steroid resistant asthma. This is the subject of the invention described herein, as elaborated upon in the disclosure which follows.

DETAILED DESCRIPTION OF PREFERRED EMBODIMENTS

The invention relates to a method for treating a steroid resistant condition via administration of gamma interferon to a subject, such as a human being, in an amount sufficient to alleviate at least one parameter of that condition.

As elaborated upon herein, the term "steroid resistant condition" refers to a form of a condition in which therapy with steroids is not as helpful as it generally is. Asthma is one example of such a condition. Generally, asthmatics can be treated with steroid drugs, but a subpopulation shows resistance to such treatment.

Parameter as used herein is synonymous with "marker" in that these terms refer to conditions, e.g., which the attending health care worker associates with a particular condition. Again, with reference to asthma, such parameters include wheezing, shortness of breath, elevated IgE levels in blood, mast cell proliferation, and so forth. All such parameters as well as others known to the skilled artisan are contemplated herein.

The following non-limitative examples demonstrate the applicability of the invention in some detail.

EXAMPLE 1

As indicated supra, persistent T cell activation is a characteristic of steroid resistant asthma. Experiments were carried out to determine if cytokines could effect the sensitivity of cells characteristic of steroid resistant asthma. To do this, known techniques including a [$^3$H]-dexamethasone radioligand binding assay and Scatchard analysis were employed. These were used to assess the number of glucorticoid receptor molecules, and their binding affinity ("Kd") on tested cells.

Peripheral blood mononuclear cells ("PBMCs") from normal donors were cultured in the presence or absence of cytokines. Specifically, interleukin-2 and interleukin-4 were added to the cells. When the interleukins were added and incubated for 48 hours, the Kd of the receptors was determined to be $35.3 \times 10^{-9} \pm 2.5$, P 0.002, as compared to controls which were much lower ($4.0 \times 10^{-9} \pm 1.0$). No significant increase was found using either IL2 or IL-4 alone (Kd $3.6\ 10^{-9} \pm 3.1$, IL-2); ($6.8 \times 10^{-9} \pm 0.7$, IL-4). When IL-2 and IL-4 were added together, the total number of receptors also increased. These observations suggested further studies to observe the functional effect of the two interleukins in pre-incubation.

EXAMPLE 2

The steroid derivative methylprednisone is known to suppress PDB/ionomycin-induced T cell proliferation and interferon gamma secretion. PBMCs were pre-incubated with the combination of IL-2 and IL-4, discussed supra, after which methylprednisone was added. As compared to controls where IL-2 and IL-4 were not added, the methylprednisone has considerably less inhibiting effect on the induced proliferation and gamma interferon secretion when there was pre-incubation.

EXAMPLE 3

The effect of the combination of IL-2 and IL-4 on glucocorticoid receptor binding affinity was discussed supra. In an additional study, gamma interferon was added. The effect of the combined interleukin was inhibited.

The reversal of the effect of IL-2 and IL-4 by gamma interferon is of interest and significance because, as indicated by example 1, supra, these two interleukins reduce the binding affinity of the glucorticoid receptors, which are essential in delivery of steroid drugs to the recipient cells. It can therefore be said that gamma interferon reverses the steroid resistance found in these cells, indicating its usefulness in a therapeutic role for steroid resistant conditions. The term "steroid resistant condition" as used herein refers to a disorder which is normally treated by administration of a steroid or steroid derived drug, but which is resistant to such treatment in at least a portion of the afflicted population.

As the art indicates, administration of gamma interferon in vivo is regarded as safe. Particular doses for the conditions described herein will vary, depending upon the individual circumstances of the patient. Generally, however, an effective amount of gamma interferon will range from about 0.01 mg/M$^2$ to about 0.5 mg/M$^2$ per day, with recombinant interferon being the preferred form of the product, recombinant human gamma interferon being especially preferred. The different forms of the cytokine given at column 10, lines 9-24 of the Ammann patent cited supra are all contemplated within this invention. The dosage given supra is the dose per day, and this dosage an be broken up into several smaller doses over the course of the day, which is preferable, or administered once.

The form by which the drug is administered may vary, again depending on dosage and condition being treated. In asthma patients, e.g., drugs are frequently administered via an oral mist or spray, as well as via nebularization. Nasal administration is also a preferred mode of delivery, as is oral administration via liquids, solids, syrups, tablets, etc. All standard forms of drug delivery are contemplated, including injection, be it subcutaneous or intravenous, time released implantation, and so forth.

The gamma interferon may also be administered in combination with other drugs, including steroids, antiallergy drugs, bronchodilators, beta adrenergic drugs, immunomodulators, other cytokines, and so forth. All forms of drug delivery and administration, and combination with other drugs for treatment of steroid resistant conditions are contemplated within the scope of this invention.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Method for treating steroid resistant asthma comprising administering an amount of gamma interferon to a patient with said steroid resistant asthma sufficient to alleviate at least one parameter associated with said steroid resistant asthma.

2. Method of claim 1, comprising administering said gamma interferon via subcutaneous injection.

3. Method of claim 1, wherein said gamma interferon is administered at a dosage ranging from about 0.01 mg/M$^2$ to about 0.5 mg/M$^2$ per day.

4. Method of claim 3, wherein said gamma interferon is administered in a plurality of administrations.

5. Method of claim 1, further comprising administering at least one non-steroid anti-asthma drug to said patient in combination with said gamma interferon.

6. Method of claim 5, wherein said asthma drug is an anti-allergy drug, a bronchodilator, a beta-adrenergic drug, an immunomodulator or a cytokine.

7. Method of claim 1, wherein said gamma interferon is administered via oral inhalation.

* * * * *